United States Patent
Abe

(10) Patent No.: US 9,298,876 B2
(45) Date of Patent: Mar. 29, 2016

(54) IMAGE PROCESSING METHOD AND IMAGE PROCESSING APPARATUS FOR REGISTERING ADDITIONAL INFORMATION OF IMAGE INFORMATION

(75) Inventor: Masahiro Abe, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 680 days.

(21) Appl. No.: 11/040,660

(22) Filed: Jan. 21, 2005

(65) Prior Publication Data

US 2005/0203954 A1    Sep. 15, 2005

(30) Foreign Application Priority Data

Feb. 5, 2004    (JP) ................. 2004-029471

(51) Int. Cl.
*G06F 19/00*    (2011.01)

(52) U.S. Cl.
CPC ............ *G06F 19/321* (2013.01); *G06F 19/322* (2013.01); *G06F 19/324* (2013.01)

(58) Field of Classification Search
CPC ... G06F 19/321; G06F 19/322; G06F 19/323; G06F 19/324; G06F 19/325; G06F 19/326
USPC ............ 707/104, 104.1; 715/700, 741, 780, 715/748, 783; 705/1, 2, 3; 700/237
See application file for complete search history.

(56) References Cited

U.S. PATENT DOCUMENTS

| 6,366,683 B1 * | 4/2002 | Langlotz ............ G06F 19/3487 128/922 |
| 6,751,603 B1 * | 6/2004 | Bauer ............... G06F 17/30067 |
| 2003/0101075 A1 * | 5/2003 | Ban et al. .......................... 705/2 |
| 2004/0024781 A1 * | 2/2004 | Youd ................ G06F 17/30985 |
| 2004/0030578 A1 * | 2/2004 | Cross ..................... G06Q 50/22 705/2 |
| 2006/0069574 A1 * | 3/2006 | Ok ................................... 705/1 |
| 2006/0087402 A1 * | 4/2006 | Manning .......... G05B 19/41875 340/3.1 |

FOREIGN PATENT DOCUMENTS

| JP | 6187381 A | * | 7/1991 |
| JP | 6-187381 A | | 7/1994 |
| JP | 06187381 A | * | 7/1994 |
| JP | 08-289875 A | | 11/1996 |
| JP | 3039378 U | | 4/1997 |
| JP | 2003-203120 A | | 7/2003 |

\* cited by examiner

Primary Examiner — Sherrod Keaton
(74) Attorney, Agent, or Firm — Canon USA, Inc. IP Division

(57) ABSTRACT

An information processing apparatus for registering additional information of an image in a storage unit reads additional information items of an input image, sets a check item condition for additional information, matches at least one of the additional information items against a corresponding additional information item registered in the storage unit according to the check item condition, and controls whether to register the additional information items in the storage unit depending on a result of the matching.

16 Claims, 16 Drawing Sheets

FIG. 10

| | | |
|---|---|---|
| ! | " | # |
| $ | % | & |
| ' | ( | ) |
| * | + | , |
| - | . | / |
| : | ; | < |
| = | > | ? |
| @ | [ | ¥ |
| ] | ^ | _ |
| ` | { | \| |
| } | ~ | |

FIG. 11

SET CHECK ITEMS

REQUIRED PATIENT INFORMATION
- ☑ PATIENT NAME (1001)
- ☑ BIRTH DATE (1002)
- ☐ SEX (1003)

ADDITIONAL INFORMATION FOR MATCHING
- ☑ PATIENT NAME (1004)
- ☑ BIRTH DATE (1005)
- ☐ SEX (1006)

1007 / 101 — ☑ USE THIRD AND SUBSEQUENT STRINGS (E. G., MIDDLE NAME) TO CHECK PATIENT NAME

1008 — [OK]

---

SET CHECK ITEMS

REQUIRED PATIENT INFORMATION
- ☑ PATIENT NAME
- ☑ BIRTH DATE
- ☐ SEX

ADDITIONAL INFORMATION FOR MATCHING
- ☐ PATIENT NAME
- ☑ BIRTH DATE
- ☐ SEX

1009 — ▨ USE THIRD AND SUBSEQUENT STRINGS (E. G., MIDDLE NAME) TO CHECK PATIENT NAME

```
┌─────────────────────────────────────────────────┐
│ SET CHECK ITEMS                                 │
├─────────────────────────────────────────────────┤
│                                                 │
│    REQUIRED PATIENT INFORMATION                 │
│      ☑ PATIENT   ☑ BIRTH     ☐ SEX              │
│         NAME        DATE                        │
│      1101         1102       1103               │
│    ADDITIONAL INFORMATION FOR MATCHING          │
│      ☐ PATIENT   ☑ BIRTH     ☐ SEX              │
│         NAME        DATE                        │
│      1104         1105       1106               │
│                                                 │
│ 1107 ─ ☑ OVERWRITE PATIENT NAME                 │
│  111 ─    (IF PATIENT NAME IS         1108      │
│            REQUIRED ENTRY)             ┌────┐   │
│                                        │ OK │   │
│                                        └────┘   │
└─────────────────────────────────────────────────┘
```

RELATIONSHIPS BETWEEN CHECKBOXES AND NOS.

IMAGE PROCESSING METHOD AND IMAGE PROCESSING APPARATUS FOR REGISTERING ADDITIONAL INFORMATION OF IMAGE INFORMATION

BACKGROUND OF THE INVENTION

1. Field of the Invention

The present invention relates to image processing methods and image processing apparatuses for registering additional information of image information, and in particular to a data matching method when information is registered. More particularly, the present invention relates to a method for registering information in a medical image database of a medical network system.

2. Description of the Related Art

The recent advent of digital X-ray apparatuses has promoted the recording of X-ray images in computers as digital data. Typical digitized image data has additional information such as patient information and examination information. A database system for managing images based on these items of information has also been developed. More specifically, a new diagnostic imaging workflow is realized, where the database is searched for a patient image based on additional information of the patient image, such as a patient ID, and the patient image is displayed on a cathode ray tube (CRT) or a liquid crystal display for diagnosis.

A general medical image database system called the Picture Archiving and Communication System (PACS) includes an image generation apparatus (modality), a file server, a database, etc., in which these components are interconnected via a network. The modality generates a medical digital image and assigns the generated medical digital image additional information, such as patient information and examination information, in accordance with the Digital Image Communication in Medicine (DICOM) standard as an image header. The generated image data is transferred via the network and saved in the file server, and the information in the image header is registered in the database.

In such a medical image database system, a plurality of images can have the same information, such as the patient name and patient ID, in the image headers. More specifically, if a patient with a patient ID "001" is examined on different days, the same patient ID and patient name are assigned to the headers of the images generated on those days. These images are registered in the database as examination data with the patient ID "001". In other words, the information in the image headers registered in the database is identified according to the patient.

In such a system, however, an operator's typing error can cause incorrect information to be registered if the system is not structured to only accept correct information.

Say that a patient name "Taro Yamada" is registered for the first radiographic examination of a patient. If "Yamada" is registered as the patient name for the second radiographic examination of the same patient, the patient name is changed from "Taro Yamada" to "Yamada" in the system, if the system allows patient names to be overwritten. This is problematic in that a search for images of the patient with a patient name "Taro Yamada" fails.

In order to overcome this problem, Japanese Patent Laid-Open No. 6-187381 describes a system for informing the user of any change in data registered in the database. In short, the user can recognize changed information in the database.

The method described in the Japanese Patent Laid-Open No. 6-187381, however, identifies data in the database by IDs, and is not capable of preventing incorrect data from being registered in the database, if the operator enters an incorrect ID.

Now, say that "Hanako Yamada" with a patient ID "15234" was examined in August 2003, and the patient information of "Hanako Yamada" was registered in the database. Furthermore, it is presumed that when "Taro Yamada" with a patient ID "12345" is examined in September 2003, he is mistakenly registered with a patient ID "15234". In short, the patient ID "15234" is registered as additional information of "Taro Yamada". Under this presumption, the information of the images acquired for "Taro Yamada" in September 2003 is registered in the database as information about "Hanako Yamada" with the patient ID "15234". As a result, a search for an image acquired in September 2003 with a patient name "Taro Yamada" and a patient ID "12345" for diagnostic imaging fails.

SUMMARY OF THE INVENTION

The present invention is intended to prevent image information from being associated with incorrect information when the image information is registered.

The present invention is also intended to efficiently determine whether information to be registered is correct.

According to one aspect of the present invention, an information processing method for registering additional information of an image in a storage unit includes: reading a plurality of additional information items of an input image; setting at least one check item condition for additional information; matching at least one of the plurality of additional information items read against a corresponding additional information item registered in the storage unit according to the at least one check item condition set; and controlling whether to register in the storage unit the plurality of additional information items read based on a result of the matching of the at least one of the plurality of additional information items.

According to another aspect of the present invention, an information processing apparatus for registering additional information of an image in a storage unit includes: an additional-information reading unit for reading a plurality of additional information items of an input image; a check-item-condition setting unit for setting at least one check item condition for additional information; an additional-information matching unit for matching at least one of the plurality of additional information items read by the additional-information reading unit against a corresponding additional information item registered in the storage unit according to the at least one check item condition set by the check-item-condition setting unit; and an additional-information registration control unit for controlling whether to register in the storage unit the plurality of additional information items read by the additional-information reading unit based on a result of matching of the at least one of the plurality of additional information items.

According to another aspect of the present invention, a control program causes a computer to execute the above-described information processing method.

According to still another aspect of the present invention, a computer-readable storage medium stores a control program for causing a computer to execute the above-described information processing method.

According to still another aspect of the present invention, an information processing apparatus includes: a reception unit configured to receive image information having additional information including a plurality of items; a selection unit configured to select at least one required item for which information needs to be entered from among the plurality of items and at least one matching item whose information needs to match corresponding stored information; a reading unit configured to read stored additional information including ID information equivalent to ID information included in the received image information; a determination unit configured to make a determination as to whether the information of the selected at least one matching item in the image information matches corresponding information in the stored additional information read by the reading unit; and a storage unit configured to store the image information by associating the image information with the additional information, if the determination made by the determination unit indicates that the information of the selected at least one matching item in the image information matches the corresponding information in the stored additional information read by the reading unit.

Further features and advantages of the present invention will become apparent from the following description of exemplary embodiments (with reference to the attached drawings).

BRIEF DESCRIPTION OF THE DRAWINGS

FIG. 10 lists examples of delimiters according to the third embodiment of the present invention.

FIG. 11 is a diagram depicting one example of a check-item-condition setting graphical user interface according to a fourth embodiment of the present invention.

FIG. 12 is a diagram depicting one example of a check-item-condition setting graphical user interface according to a fifth embodiment of the present invention.

DESCRIPTION OF THE EMBODIMENTS

Exemplary embodiments according to the present invention will now be described with reference to the drawings.

First Embodiment

Figure 1:
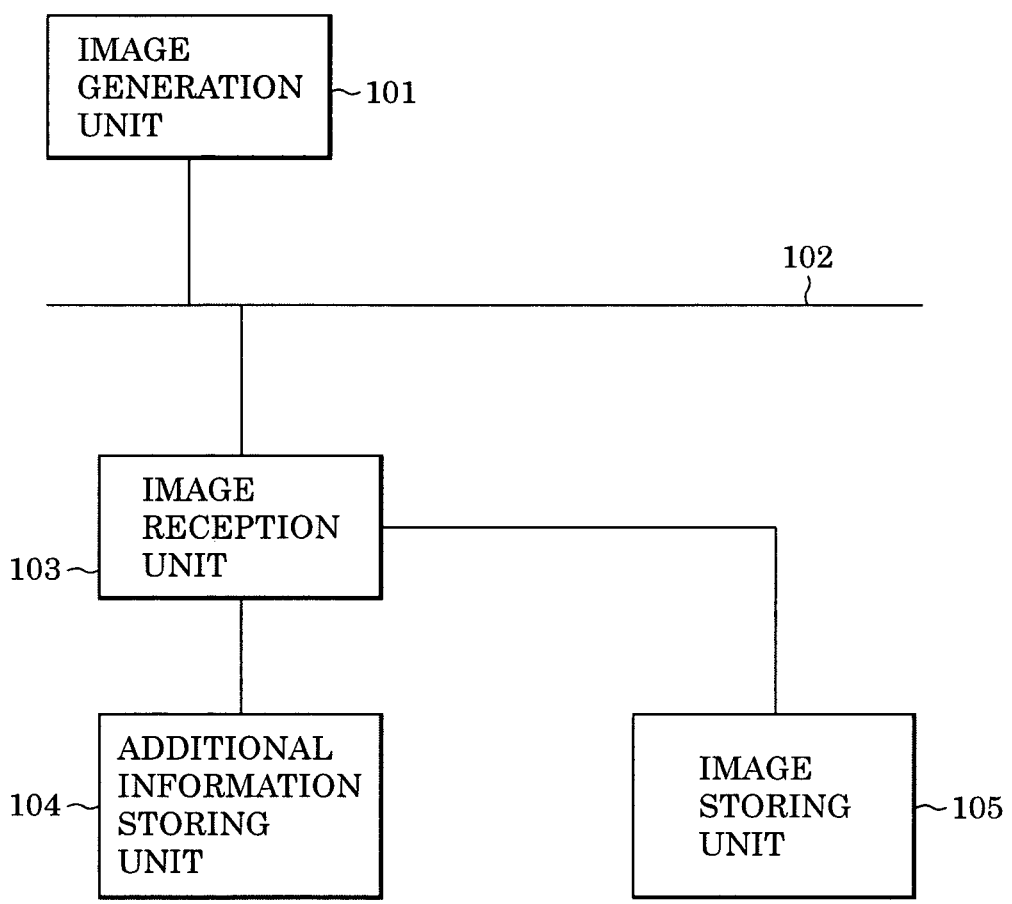
FIG. 1 is a block diagram depicting the structure of a data registration system according to a first embodiment of the present invention.

FIG. 1 is a block diagram depicting the structure of a data registration system according to a first embodiment of the present invention.

The data registration system according to the first embodiment includes an image generation unit 101, an image reception unit 103, an additional information storing unit 104, and an image storing unit 105. These units are interconnected via a network 102.

The image generation unit 101 is generally realized by a diagnostic X-ray system, an X-ray CT scanner, a magnetic resonant imaging (MRI) system, a diagnostic ultrasound system, or a fundus camera. The image generation unit 101 generates medical image data and assigns the generated medical digital image additional information, such as patient information and examination information, as an image header.

The image reception unit 103 receives via the network 102 the image provided with the additional information generated by the image generation unit 101. The image reception unit 103 is realized by a general-purpose computer including at least an input device such as a mouse and a keyboard and an output device such as a cathode ray tube (CRT) or a liquid crystal display (LCD).

The additional information storing section 104 saves the additional information of the image received in the image reception unit 103. The additional information storing section 104 is realized by, for example, a database built in the image reception unit 103. The image storing unit 105 saves the image received in the image reception unit 103. The image storing unit 105 is realized by, for example, a storage medium such as a hard disk and a non-volatile memory provided in the image reception unit 103.

Although the system shown in FIG. 1 includes one image generation unit 101, the system may include a plurality of image generation units 101. Furthermore, the additional information storing section 104 and the image storing unit 105 are not limited to those described in FIG. 1. The additional information storing section 104 and the image storing unit 105 may be realized by, for example, storage sections in a different computer connected to the image reception unit 103 via a different network.

Figure 2:
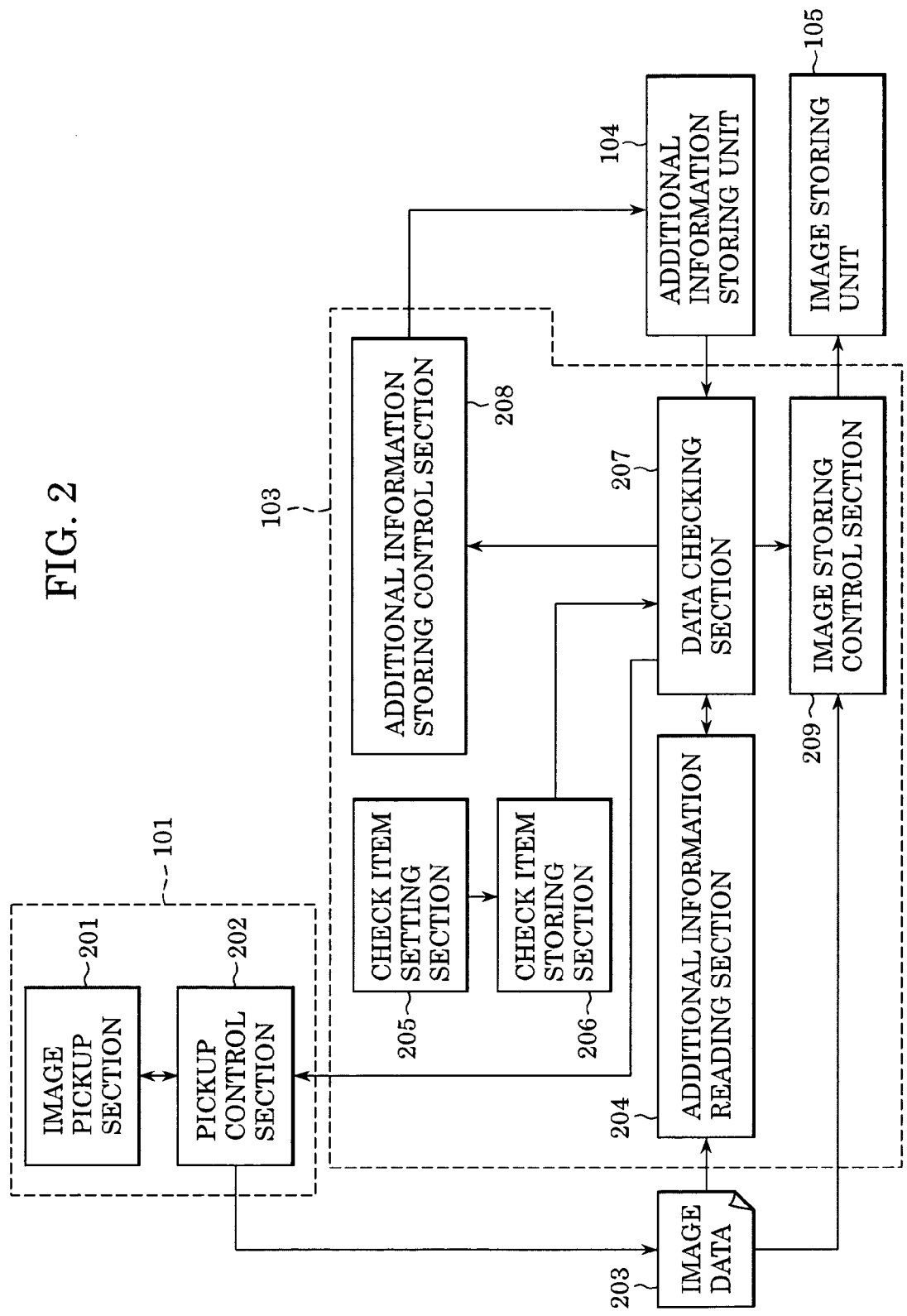
FIG. 2 is a block diagram depicting a functional structure of a data registration system according to the first embodiment of the present invention.

The functional structure according to the first embodiment of the present invention will now be described. FIG. 2 is a diagram depicting a functional structure of the data registration system according to the first embodiment of the present invention.

Referring to FIG. 2, the image generation unit 101 includes an image pickup section 201 for acquiring images. The image generation unit 101 further includes a pickup control section 202 for controlling image acquisition by the image pickup section 201. The pickup control section 202 is a terminal including a mouse, a keyboard, and a display unit.

As described above, the image reception unit 103 in FIG. 1 receives image data 203 acquired by the image pickup section 201. An additional information reading section 204 reads out patient information and examination information accompanying the image data 203.

A check item setting section 205 sets check item conditions. Check item conditions specify the items to be matched against the database according to certain conditions. A check item storing section 206 stores the check item conditions set by the check item setting section 205.

A data checking section 207 compares the additional information read out by the additional information reading section 204 with the information acquired from the additional information storing section 104 based on the check item conditions stored in the check item storing section 206 to determine whether the check item conditions are satisfied. Furthermore, the data checking section 207 includes an interface for enabling communication with the pickup control section 202 so that the determination result can be reported to the image generation unit 101.

An additional information storing control section 208 registers in the additional information storing section 104 the additional information read out by the additional information reading section 204, if the data checking section 207 determines that the check item conditions are satisfied. An image storing control section 209 saves the received image data 203 in the image storing unit 105, if the data checking section 207 determines that the check item conditions are satisfied.

The above described sequence of processing from image reception to image registration will now be described.

Figure 3:
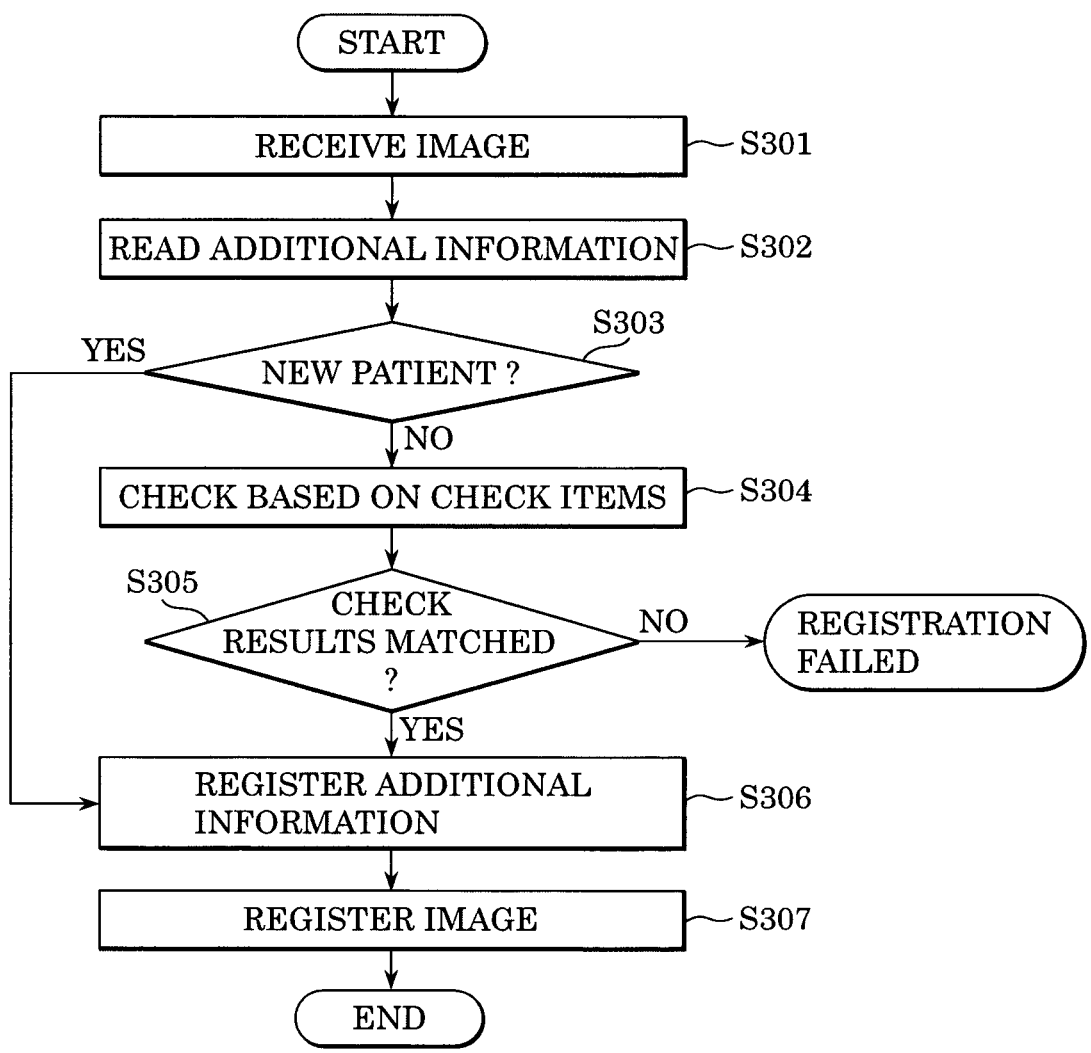
FIG. 3 is a flowchart illustrating the processing from image reception to data registration according to the first embodiment of the present invention.

FIG. 3 is a flowchart illustrating the processing from image reception to image registration according to the first embodiment of the present invention. FIG. 3 shows a typical example of processing from image reception to image registration by the data registration system according to the first embodiment.

First, an X-ray image of a certain patient is generated in the image generation unit 101, and is transferred to the image reception unit 103 via the network 102.

In step S301, the image reception unit 103 receives the transferred image. Then, in step S302, the additional information of the received image is read by the additional information reading section 204. The additional information read by the additional information reading section 204 is patient information such as the patient ID, the patient name, the sex of the patient, and the birth date of the patient.

Next, in step S303, reference is made to the additional information storing section 104 for the patient information of the received image.

More specifically, the data checking section 207 checks whether the patient ID read out in step S302 exists in the additional information storing section 104. If the patient ID does not exist, the patient with the patient ID is registered as a new patient and the flow proceeds to step S306. If the patient ID exists, the flow proceeds to step S304.

In step S304, the data checking section 207 reads out check item conditions saved in the check item storing section 206, and compares the patient information of the received image with the patient information stored in the additional information storing section 104 based on the check item conditions.

In step S305, the result of the comparison is determined. More specifically, if the comparison result indicates that the check item conditions are satisfied, the flow proceeds to step S306. If the comparison result indicates that the check item conditions are not satisfied, registration processing is terminated. In this case, the system operator is informed of the cause of unsuccessful registration.

Figure 6:
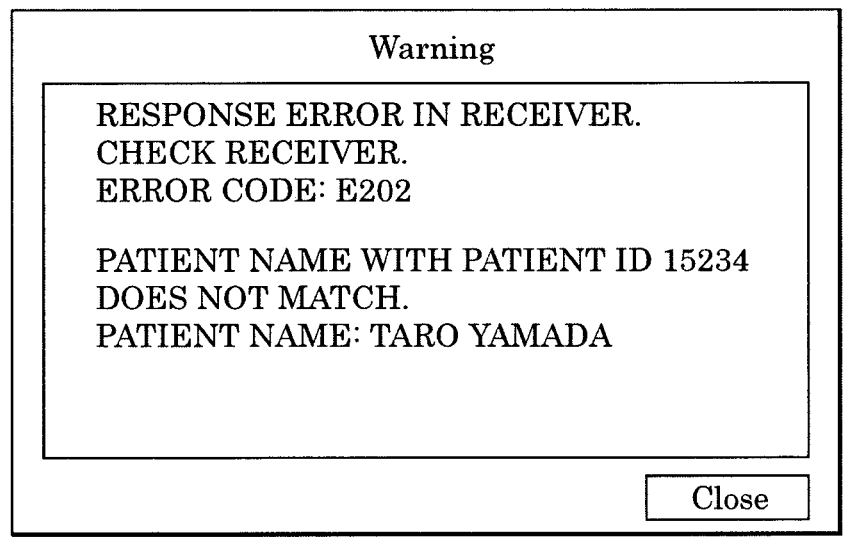
FIG. 6 is a diagram showing an example message indicating unsuccessful data matching according to the first embodiment of the present invention.

More specifically, an error message as shown in FIG. 6 is displayed on the display unit connected to the pickup control section 202. Details of the message in FIG. 6 are described later.

In step S306, the additional information storing control section 208 registers the read-out additional information in the additional information storing section 104, and the flow proceeds to step S307. More specifically, the patient information and examination information read out from the image are registered in the database. Finally in step S307, the image storing control section 209 registers the received image in the image storing unit 105 by associating the received image with the additional information saved in step S306. Check item conditions and the checking procedure are described in detail below.

Figure 4:
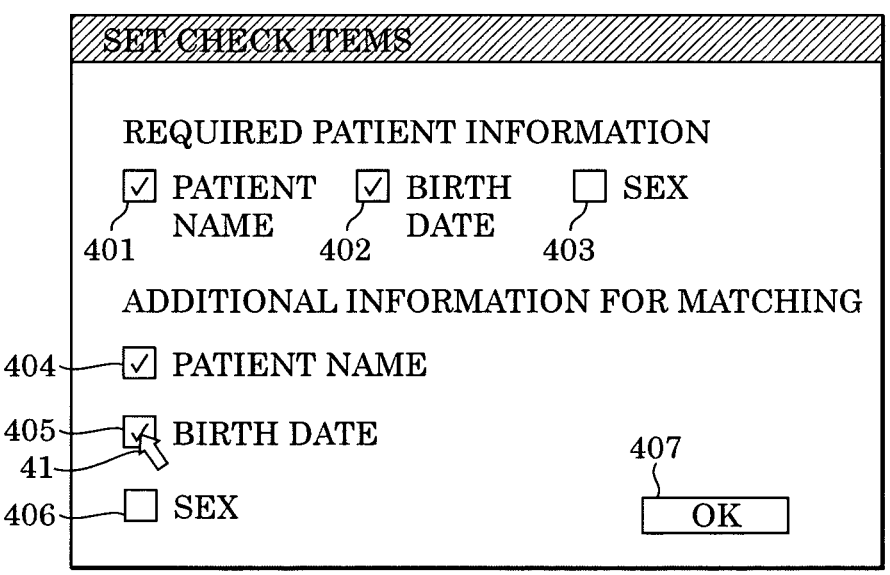
FIG. 4 is a diagram depicting one example of a check-item-condition setting graphical user interface according to the first embodiment of the present invention.

The procedure for setting check item conditions will now be described with reference to FIG. 4. FIG. 4 is a diagram showing one example of a check-item-condition setting graphical user interface (hereinafter, referred to as a GUI). This GUI is displayed on the display unit such as a CRT and a liquid crystal display connected to the image reception unit 103.

The GUI shown in FIG. 4 includes checkboxes 401 to 406 for setting check item conditions and an operation button 407 for confirming the check item conditions. To check the checkboxes 401 to 406, the operator moves a pointer 41 with a mouse onto a desired checkbox and clicks the checkbox. To uncheck, the operator clicks the checked checkbox.

The checkboxes 401 to 403 arranged in the upper part of the GUI in FIG. 4 are used to specify required entries of the patient information. In the example shown in FIG. 4, the checkbox 401 for the patient name and the checkbox 402 for the birth date are checked. In other words, the patient name and the birth date are required entries and must be entered as additional information of the received image to register the corresponding image data. In short, data checking fails if the patient name or the birth date is not entered.

On the other hand, the checkbox 403 for the sex is unchecked. That is, the sex of the patient as additional information of the received image can be omitted without causing data registration to fail.

The checkbox 404 for the patient name and the checkbox 405 for the birth date are checked. This indicates that the patient name and the birth date only are matched against the database, and the sex of the patient is not matched against the database. To confirm the settings, the operator clicks the operation button 407 with the pointer 41 placed on the operation button 407. This causes the system accept the set check item conditions.

As described above, the GUI is provided with checkboxes and an operation button. It should be noted, however, that the structure of the GUI including the layout of the checkboxes and the operation button is not limited to that shown in FIG. 4. Instead, any GUI that enables the user to specify check item conditions is acceptable.

Figure 5:
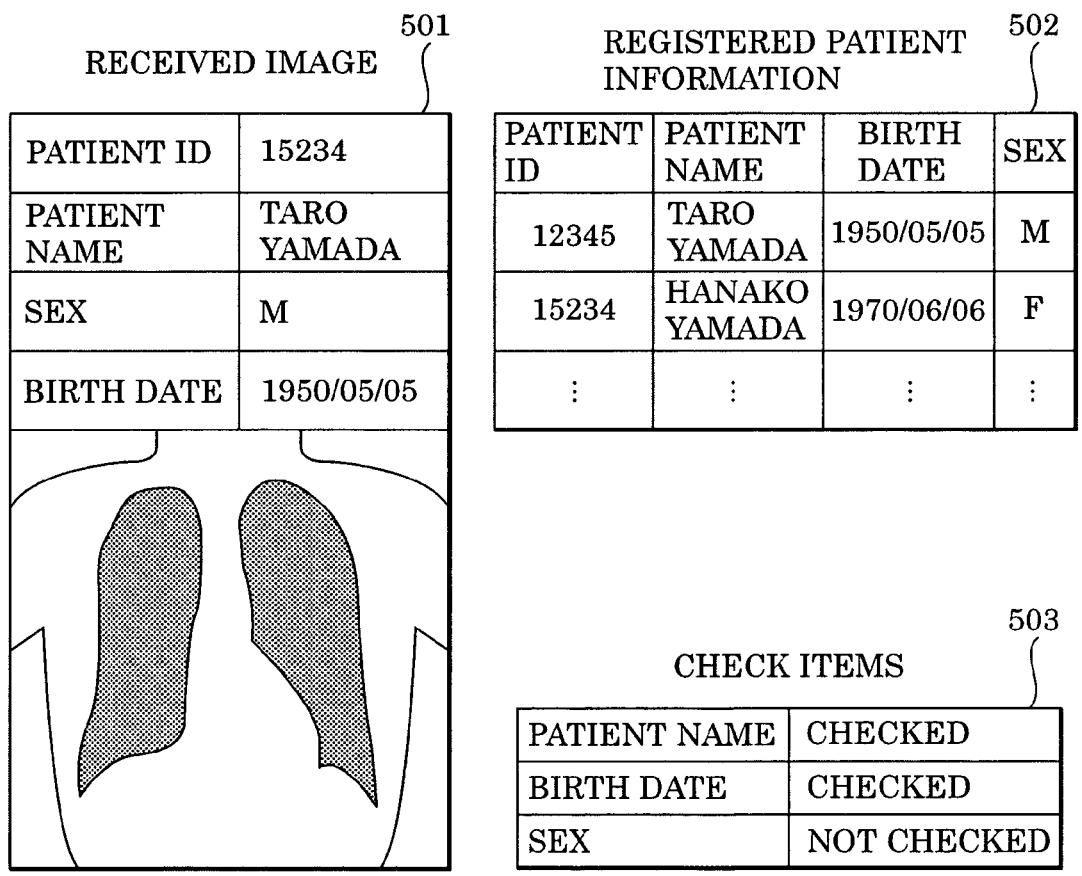
FIG. 5 is a diagram depicting one example of various data information according to the first embodiment of the present invention.

FIG. 5 shows a received image 501, registered patient information 502, and check item conditions 503 set by the check item setting section 205. The received image 501 includes patient information as part of its additional information. Here, it is presumed that the patient ID included as additional information of the received image 501, which in fact should be "12345", has been registered as "15234" due to an incorrect operation of the operator at the time of image acquisition. On the other hand, a patient ID "15234" already exists as registered patient information.

In this case, it is determined in step S303 in FIG. 3 that the patient in question is not a new patient, and hence the flow proceeds to step S304. In step S304, data matching is performed based on the check item conditions. As indicated in the check item conditions 503, the patient name and the birth date are checked (matched) against the database, and the sex is not checked. In other words, based on these check item conditions, at least the patient name and the birth date must match with the database to allow data registration processing to be completed successfully.

In the example in FIG. 5, the patient name "Taro Yamada" with the patient ID "15234" in the received image 501 does not match the patient name "Hanako Yamada" with the same patient ID in the registered patient information 502. Similarly, the birth date "May 5, 1950" with the patient ID "15234" in the received image 501 does not match the birth date "Jun. 6, 1970" with the same patient ID in the registered patient information 502. The sexes with the patient ID "15234", which are "M" in the received image 501 and "F" in the registered patient information 502, do not match. However, this mismatch is not checked because the sex is excluded from the check item conditions. As a result, since the patient name and the birth date do not satisfy the check item conditions, the data registration processing fails and is terminated.

FIG. 6 shows a warning message displayed on the pickup control section 202 if data registration terminates due to a failure. The warning message in FIG. 6 indicates that data registration has been terminated because the patient name of the image transferred from the image generation unit 101 does not match the patient name with the registered patient ID "15234". With this message displayed on the image generation unit 101 when the image reception unit 103 terminates data registration, the operator is informed of possible entry of incorrect patient information at the time of image acquisition.

As described above, the first embodiment prevents an image from being associated with an incorrect patient resulting from entry of an incorrect patient ID when the image is registered.

Second Embodiment

In the first embodiment, images are transferred via the network 102 from the image generation unit 101. However, images stored in an off-line medium, such as an MO (magneto-optical), a CD-ROM (compact disk-read-only memory), a CD-R (CD-recordable), a CD-RW (CD-rewritable), a DVD-RAM (digital versatile disk-random-access memory), a DVD-ROM, a DVD-R, and a DVD-RW, can also be read out and subjected to data matching at the time of data registration to prevent incorrect data registration.

Figure 7:
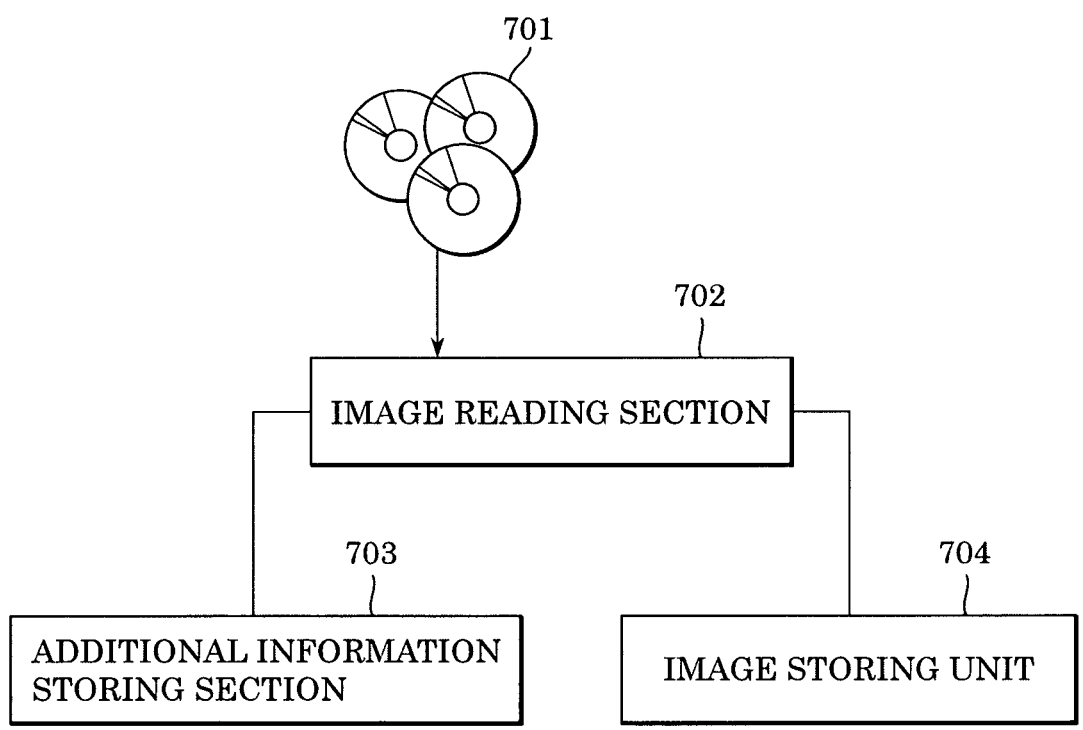
FIG. 7 is a system block diagram of a data registration system according to a second embodiment of the present invention.

FIG. 7 is a system block diagram depicting an example structure according to a second embodiment of the present invention. The data registration system according to this embodiment includes an image recording medium 701, an image reading section 702, an additional information storing section 703, and an image storing unit 704. The image recording medium 701 is generally realized by a flexible disk, an MO, a CD-ROM, a CD-R, a CD-RW, a DVD-RAM, a DVD-ROM, a DVD-R, or a DVD-RW. The image recording medium 701 stores image data including additional information such as patient information and examination information.

The image reading section 702 reads out an image recorded on the image recording medium 701. More specifically, the image reading section 702 is a general-purpose computer including at least an input device such as a mouse and a keyboard and an output device such as a CRT or LCD.

The additional information storing section 703 saves additional information of the image received in the image reading section 702. The additional information storing section 703 is realized by, for example, a database built in the image reading section 702. The image storing unit 704 saves the image read out by the image reading section 702. The image storing unit 704 is realized by, for example, a recording medium such as a hard disk and a non-volatile memory provided in the image reading section 702.

The function of the image reading section 702 in FIG. 7 corresponds to that of the image reception unit 103 in FIG. 2 according to the first embodiment.

Here, the series of processing from image reading to image registration is the same as that in the first embodiment. If data registration is terminated because the check item conditions are not satisfied at the time of data matching after image reading, a warning message is displayed on a display unit such as a CRT or an LCD connected to the image reading section 702.

Figure 8:
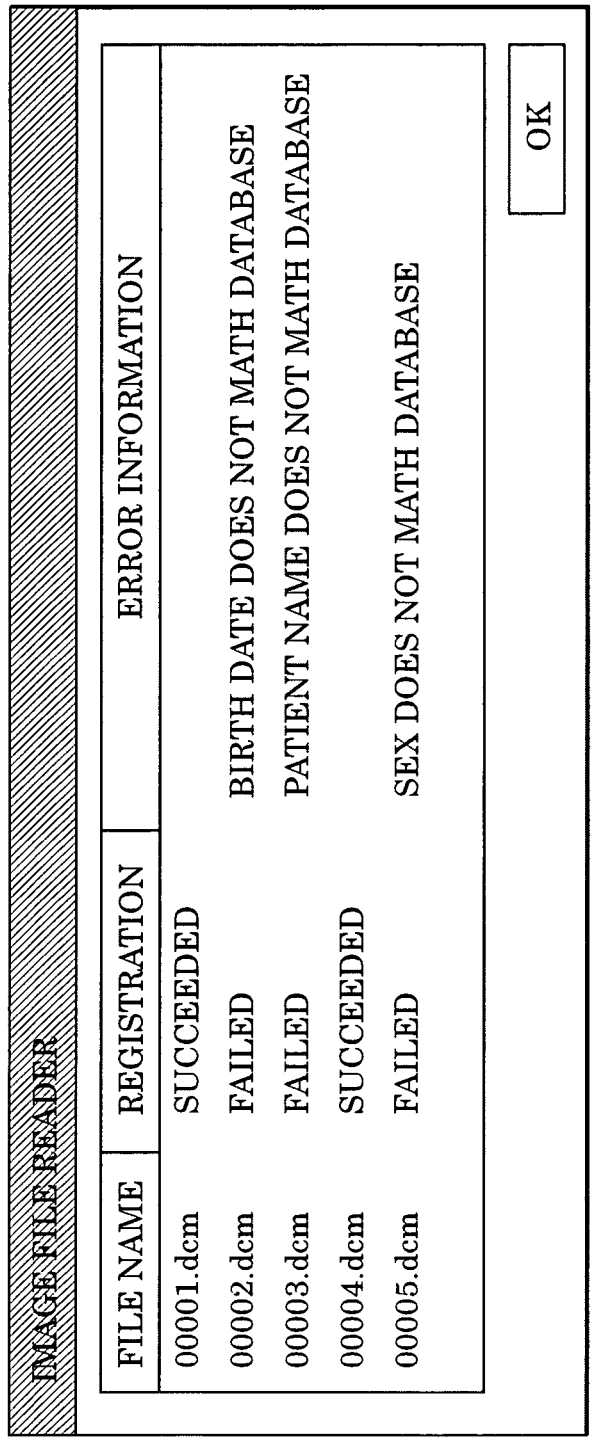
FIG. 8 is a diagram showing an example message indicating unsuccessful data matching according to the second embodiment of the present invention.

One example of a warning message displayed in this case is shown in FIG. 8.

When images are to be read out from an off-line medium, the name of any image file whose registration has failed at the time of image reading and the cause of the failure can be displayed in the form of error information in order to inform the user that image registration has failed.

In the example in FIG. 8, messages indicating that the patient name, the birth date, and the sex do not match the database are displayed as error information. However, any type of information, including a message indicating that the third string of the patient name does not match, as described below, is acceptable, as long as the user is informed of the cause of unsuccessful data registration.

Third Embodiment

In the first embodiment, the patient information is matched against the database to check whether both the patient name and the birth date completely match the corresponding patient information in the database. A patient name, however, generally includes a given name and a family name separated by a delimiter such as a space. In other words, the operator enters a delimiter such as a space between the given name and the family name when the patient is registered for image acquisition.

In this case, if the entire patient name, as one string, is matched against the database, the result may indicate a matching failure depending on the number of spaces between the given name and the family name.

In other words, despite the given name and family name being correct individually, matching of the entire patient name as a single string may fail. If this is the case, the user feels inconvenient because the user must pay attention to the delimiter and the number of delimiters when entering a patient name, and must correct the patient name each time data matching fails due to the delimiter. This problem can be solved by performing the matching of patient name part by part.

Details of this part-by-part patient name matching will now be described.

Figure 9:
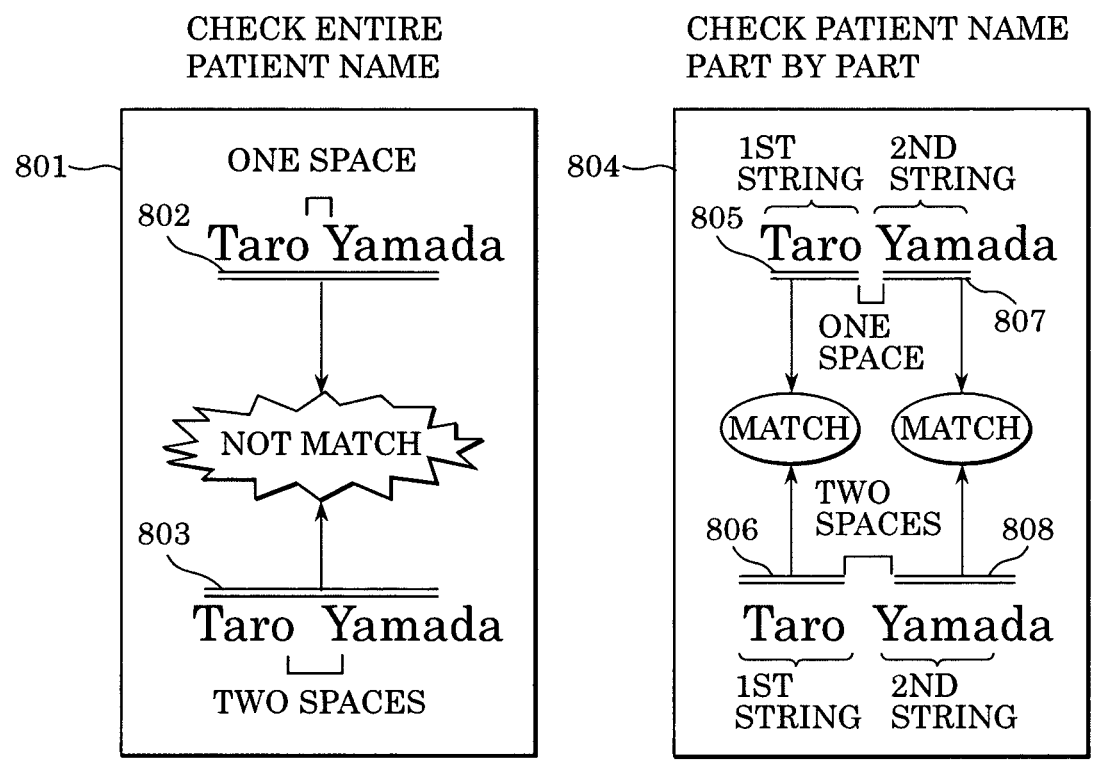
FIG. 9 is a diagram illustrating part-by-part matching of a patient name according to a third embodiment of the present invention.

FIG. 9 is a diagram illustrating part-by-part patient name matching according to a third embodiment of the present invention.

A matching scheme 801 shows an example in which the entire patient name is regarded as one character string to perform patient name matching. In the matching scheme 801, a character string 802 representing a first patient name has one space between the given name and the family name, whereas a character string 803 representing a second patient name has two spaces between the given name and the family name.

According to the matching scheme 801, when the first patient name 802 is matched against the second patient name 803, the first patient name 802 is determined to be different from the second patient name 803 due to the difference in the number of spaces between the given name and the family name, resulting in a matching failure.

On the other hand, in a matching scheme 804, the given name and the family name are checked separately when patient name matching is performed. A character string 805 represents a first character string of a first patient name, and a character string 806 represents a first character string of a second patient name. In general, the character strings 805 and 806 each correspond to the given name of the patient name.

A character string 807 represents a second character string of the first patient name, and a character string 808 represents a second character string of the second patient name. In general, the character strings 807 and 808 each correspond to the family name of the patient name.

As shown in FIG. 9, according to the matching scheme 804, the character string 805 is matched against the character string 806, and the character string 807 is matched against the character-string 808. This matching scheme 804 causes the matching result to be successful regardless of the type of the delimiter or the number of delimiters used between the given name and the family name.

As a result, the problem in which matching results in a failure due to the delimiter (which functions just as a separating character that is not an integral part of the patient name) is overcome.

Figure 10:
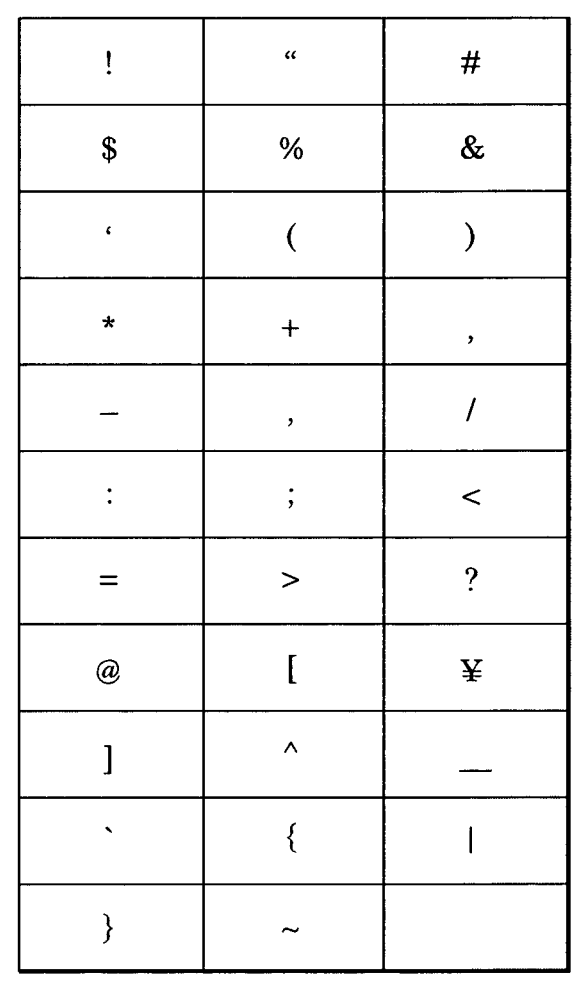

According to the third embodiment, a space is used as a delimiter between the given name and the family name. The delimiter, however, is not limited to a space, and may be a character, such as those shown in the example in FIG. 10. These special characters are not used as part of a typical person's name.

Fourth Embodiment

The third embodiment has been described by way of an example appropriate for processing a typical Japanese name. Names other than Japanese names, for example, European names may have a middle name and/or a name suffix, such as Jr., and may need to be processed differently. According to a fourth embodiment of the present invention, the third embodiment is extended to extract up to the third character string of a patient name and to perform matching of the first to the third strings of the patient name part by part.

A middle name may be entered in the form of an initial in some cases. The system may be modified such that if the second character string of an entered patient name includes only one character, the second character string is matched against the initial character of the second character string of the corresponding patient name in the database.

If the patient name includes three or more delimiters, the patient name may be divided into four or more parts for matching. This may take a long time to process the patient name, because the patient name needs to be divided for matching each time a delimiter is encountered.

For this reason, in practice, the fourth and the subsequent characters, which are not so significant to perform matching of the patient name, can be integrated into the third character string. This prevents the patient name from being divided into four or more parts, even if the patient name contains three or more delimiters, and consequently the processing time can be reduced.

At this time, as shown in FIG. 11, the check-item-condition setting GUI may be designed to contain a checkbox 1007 for allowing the user to select whether the third and subsequent characters are used for matching of the patient name.

Furthermore, the GUI is designed such that with the patient name de-selected from additional information for matching, i.e., with the checkbox 1004 unchecked the checkbox 1007 is automatically unchecked and disabled, as shown with a checkbox 1009, so that the user cannot access the checkbox 1007. This technique prevents the user from specifying inconsistent settings between the checkboxes 1004 and 1007.

Figure 14:
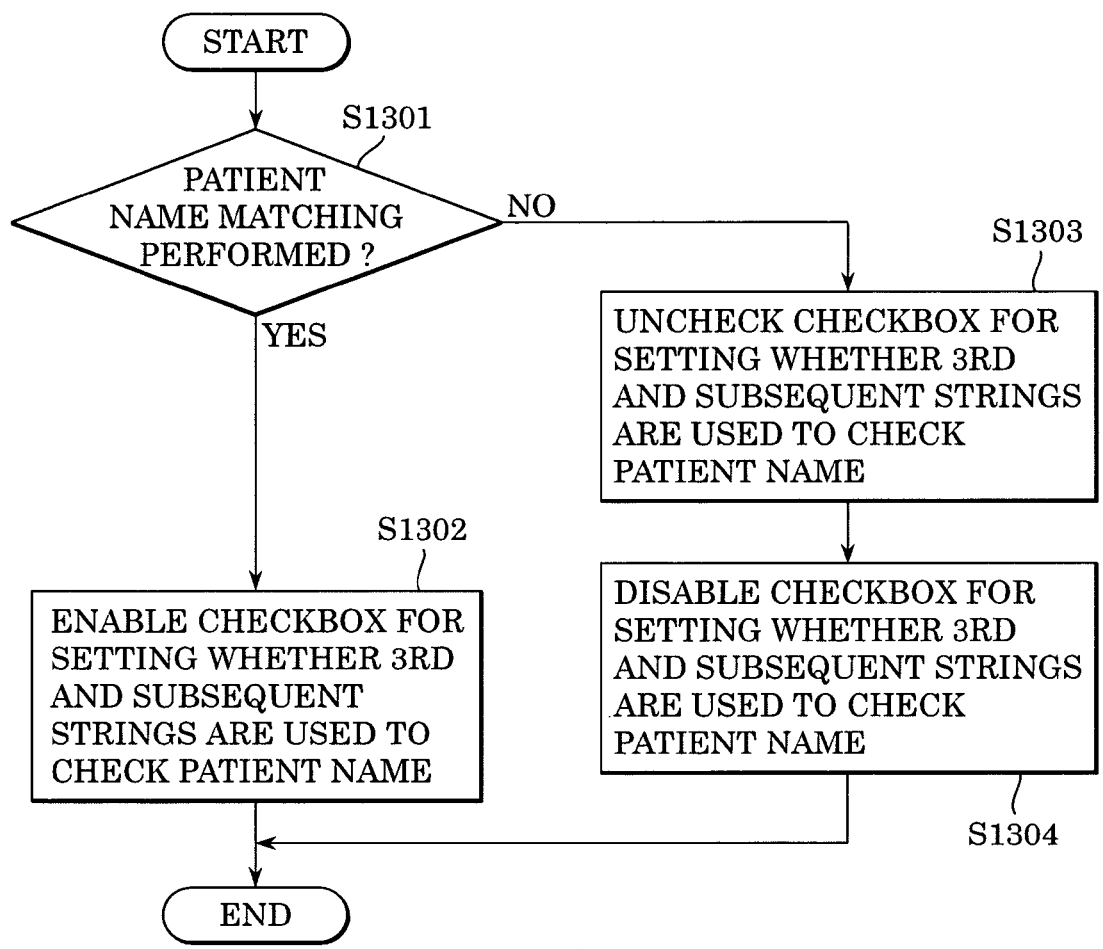
FIG. 14 is a flowchart illustrating the processing performed with a check-item-condition setting graphical user interface according to the fourth embodiment of the present invention.

FIG. 14 is a flowchart illustrating the processing when access to a checkbox is controlled on the check-item-condition setting GUI shown in FIG. 11 according to the fourth embodiment. This processing flow is triggered when the user checks or unchecks the checkbox 1004 for setting whether the patient name is used for matching. In step S1301, the flow proceeds to step S1302 if the checkbox 1004 is checked or to step S1303 if the checkbox 1004 is unchecked.

In step S1302, the checkbox 1007 for setting whether the third character string is used for matching of the patient name is enabled to allow the user to access the checkbox 1007. In contrast, in step S1303, the checkbox 1007 is unchecked, and the flow proceeds to step S1304. In step S1304, the checkbox 1007 is disabled to prevent the user from accessing the checkbox 1007.

Fifth Embodiment

The patient name may change due to marriage, divorce, or adoption. In such a case, with the matching schemes according to the first to the fourth embodiments, matching of the patient name results in a failure because the family name itself is changed, even if the delimiter is processed appropriately.

According to a fifth embodiment of the present invention, this problem is solved by exercising ingenuity in setting check item conditions, so that a new family name can be registered without changing the existing family name.

The fifth embodiment will now be described in detail with reference to FIG. 12.

FIG. 12 is one example of a check-item-condition setting GUI for avoiding patient name matching for a patient whose name has been changed, while still preventing incorrect data registration resulting from entry of an incorrect patient ID.

First, in order to process a family name changed due to, for example, marriage, the patient name must be set as a required entry, i.e., the checkbox 1101 must be checked. The checkbox 1102 for the birth date and the checkbox 1103 for the sex can be checked or unchecked.

Here, if the patient name is specified as information to be checked, i.e., the checkbox 1104 for the patient name is checked, matching fails because the entered family name does not match the family name of the patient already registered in the database. For this reason, the checkbox 1104 for the patient name must be unchecked.

If neither the patient name nor the birth date is matched against the database, entry of an incorrect patient ID causes the patient to be registered as associated with another patient. To avoid this, the checkbox 1105 for the birth date must be checked. The checkbox 1106 for the sex may be checked or unchecked. Finally, the checkbox 1107 for allowing the patient name to be overwritten is checked to overwrite the patient name in the database with the new family name. This causes the patient to be registered with the new family name assigned as a result of the marriage.

Although the GUI is provided with checkboxes and an operation button as shown in FIG. 12, it should be noted, however, that the structure of the GUI including the layout of the checkboxes and the operation button is not limited to that shown in FIG. 12. Instead, any GUI that enables the user to specify check item conditions is acceptable.

Figure 15:
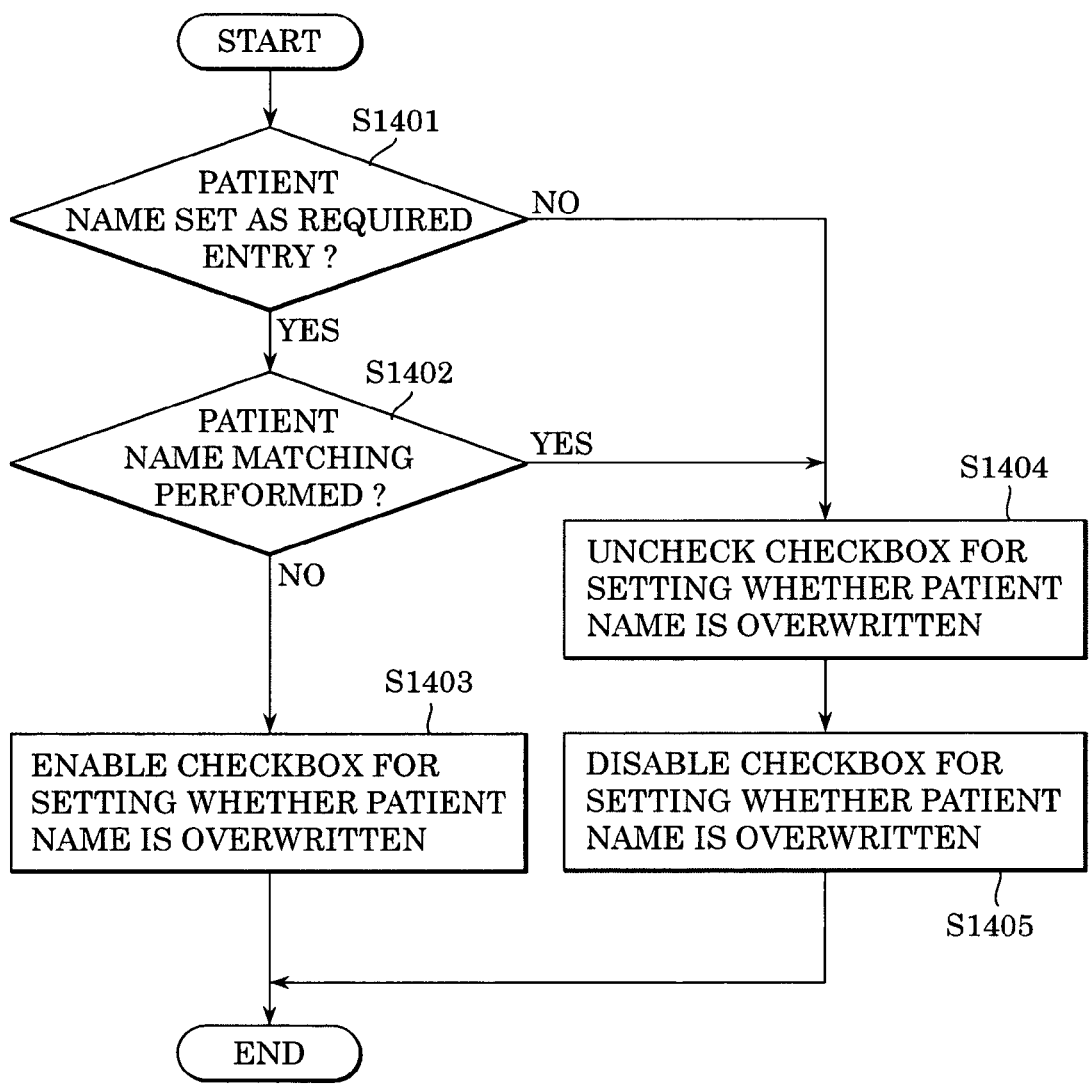
FIG. 15 is a flowchart illustrating the processing performed with a check-item-condition setting graphical user interface according to the fifth embodiment of the present invention.

FIG. 15 is a flowchart illustrating the processing when access to a checkbox is controlled on the check-item-condition setting GUI shown in FIG. 12 according to the fifth embodiment. This processing flow is triggered when the operator checks or unchecks the checkbox 1101 for selecting whether to set the patient name as a required entry.

In step S1401, the processing flow proceeds to step S1402 if the checkbox 1104 is checked or to step S1404 if the checkbox 1104 is unchecked. In step S1402, the processing flow proceeds to step S1404 if the checkbox 1104 for setting whether to match the patient name against the database is checked or to step S1403 if the checkbox 1104 is unchecked.

In step S1403, the checkbox 1107 for setting whether to overwrite the patient name is enabled to allow the user to access the checkbox 1107. In contrast, in step S1404, the checkbox 1107 is unchecked, and the flow proceeds to step S1405. In step S1405, the checkbox 1107 is disabled to prevent the user from accessing the checkbox 1107.

Sixth Embodiment

The first to fifth embodiments have been described by way of an example where the user is basically free to set check item conditions on the GUI. According to a sixth embodiment, in order to enable complicated and consistent check item conditions to be set easily, access to checkboxes is controlled to enable or disable checkboxes appropriately.

Figures 13A, 13B:
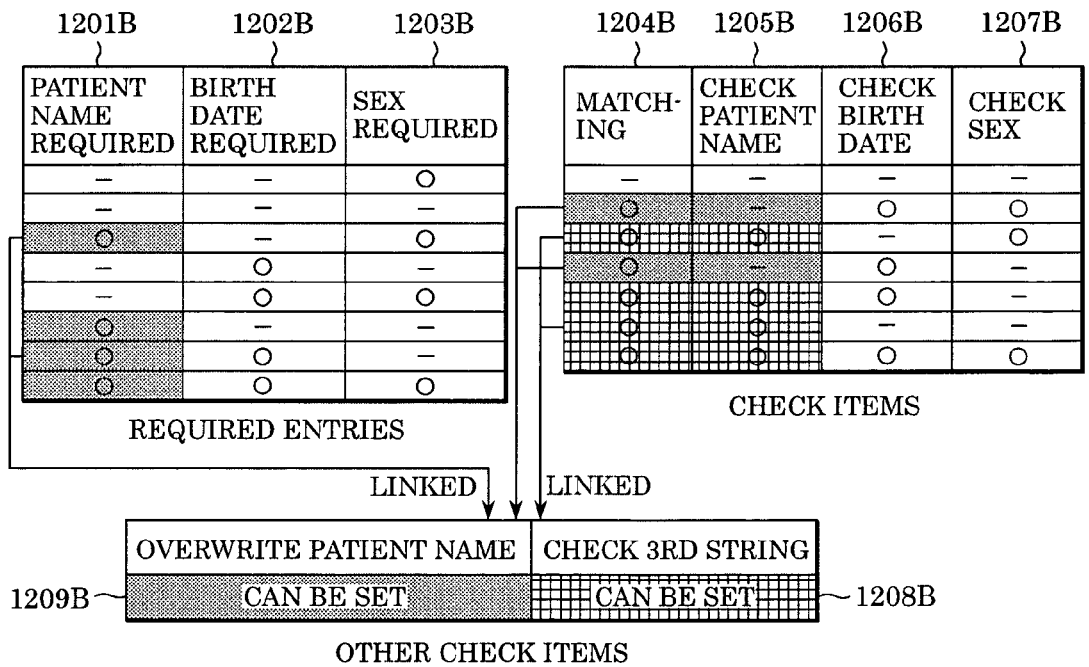
FIG. 13A is a diagram depicting one example of a check-item-condition setting graphical user interface according to a sixth embodiment of the present invention.
FIG. 13B includes tables showing combinations of check-item-conditions according to the sixth embodiment of the present invention.

The sixth embodiment will now be described with reference to FIGS. 13A and 13B. FIG. 13A shows one example of a check-item-condition setting GUI according to the sixth embodiment. FIG. 13B includes tables showing the relationships between accessibility to certain check items and combinations of settings of other check items.

Checkboxes in FIG. 13A and table columns in FIG. 13B denoted with the same numbers indicate the same check items.

Checkboxes 1201A to 1203A in FIG. 13A are selected when the corresponding items are to be set as required entries. That is, if all of these checkboxes are selected, the patient name (1201A), the birth date (1202A), and the sex (1203A) must be entered to register the patient. As shown in the table "required entries" in FIG. 13B, a total of seven combinations of the patient name, birth date, and sex are available to specify required entries: three entries with each one requiring one of the three types of data; three entries with each requiring a combination of two of the types of data; and one entry requiring all three of the types of data.

The checkbox 1204A specifies whether to use information other than the patient ID as a check item condition. The user can access the checkboxes 1205A to 1207A only if the checkbox 1204A is checked. In other words, whether the checkboxes 1205A to 1207A can be accessed depends on whether the checkbox 1204A is checked or unchecked. This relationship is shown in FIG. 13B. More specifically, circles in the column 1204B of the table "check items" in FIG. 13B indicate that the checkbox 1204A is checked. In contrast, the first row without a circle in the column 1204B has all of the patient name, birth date, and sex unchecked.

As shown in the table "check items" in FIG. 13B, according to the sixth embodiment, it is necessary that at least one of the patient name and the birth date be set as matched against the database. This is because if only the sex is used for matching of the patient information, patients with the same sex are regarded as the same patient. This is problematic in that patients cannot be identified.

For this reason, if the user checks the checkbox 1204A, at least one of the checkbox 1205A and the checkbox 1206A must be checked. To apply this requirement automatically, the check-item-condition setting GUI may be designed such that if one of the checkbox 1205A and the checkbox 1206A is unchecked, the other checkbox is automatically checked, and furthermore, the user is prevented from accessing the checkbox once the checkbox is checked.

The checkbox 1208A for setting whether to use the third character string when the patient name is matched against the database, as shown in FIG. 13B, can be checked only after the checkboxes 1204A and 1205A have been checked. As a result, it can be selected whether up to the second string is used or the third string is included for the matching of the patient name.

Furthermore, FIG. 13A shows a checkbox 1209A for setting whether to overwrite the patient name, allowing for a case where the patient name is changed because of, for example, marriage. This checkbox 1209A, as shown in FIG. 13B, can be checked to allow the patient name to be overwritten provided that the patient name is set as a required entry, matching is performed, and the patient name is not matched against the database. In other words, the checkbox 1209A can be checked only if the checkbox 1201A and the checkbox 1204A are checked and the checkbox 1205A is unchecked.

Figure 16:
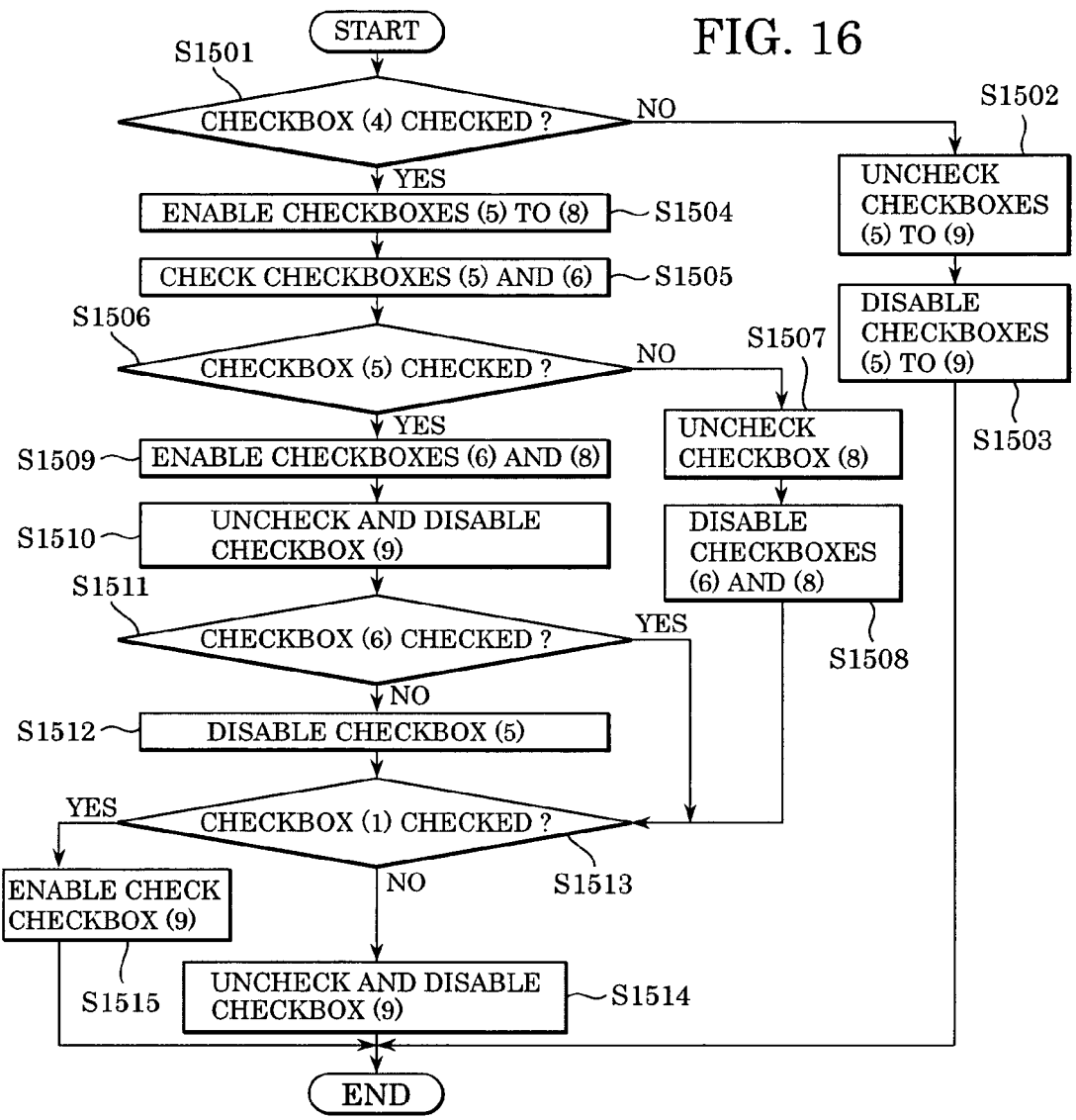
FIG. 16 is a flowchart illustrating the processing performed with a check-item-condition setting graphical user interface according to the sixth embodiment of the present invention.

FIG. 16 is a flowchart illustrating the processing when access to checkboxes is controlled on the check-item-condition setting GUI shown in FIG. 13A according to the sixth embodiment. The GUI used with the processing shown in FIG. 16 is the same as the GUI shown in FIG. 13A, except that the checkboxes are assigned sequential numbers in parentheses to make the description of the flow in FIG. 16 understood easily. In other words, checkboxes 1204A-1209A in FIG. 13A are simply referred to as 4-9, respectively, in the flowchart of FIG. 16. The flow in FIG. 16 is triggered when the user checks or unchecks the checkbox (4). In step S1501, the processing flow proceeds to step S1504 if the checkbox (4) is checked or to step S1502 if the checkbox (4) is unchecked.

In step S1502, checkboxes (5) to (9) are unchecked, and the flow proceeds to step S1503. In step S1503, the checkboxes (5) to (9) are disabled to prevent the user from accessing the checkboxes (5) to (9). At this time, the user can access checkboxes (1) to (3) only. The setting of check item conditions ends when the user clicks the OK button.

In contrast, in step S1504, the checkboxes (5) to (8) are enabled, and the flow proceeds to step S1505. In step S1505, the checkboxes (5) and (6) are automatically checked, and the flow proceeds to step S1506. This enables the patient name and the birth date to be automatically selected for matching by default when the user determines that the patient information is matched against the database.

In step S1506, the flow of processing proceeds to step S1509 if the checkbox (5) is checked or to step S1507 if the checkbox (5) is unchecked. In step S1507, the checkbox (8) is unchecked, and the flow proceeds to step S1508. In step S1508, the checkboxes (6) and (8) are disabled, and the flow proceeds to step S1513. Because of this, even if the patient name is deselected from matching, at least the birth date is included for matching when the patient information is matched against the database.

Furthermore, this prevents a contradictory situation in which the third string of the patient name is used for matching while the patient name itself is excluded from matching. In contrast, in step S1509, the checkboxes (6) and (8) are enabled, and the flow proceeds to step S1510. In step S1510, the checkbox (9) is unchecked and disabled, and the flow proceeds to step S1511.

In step S1511, the flow proceeds to step S1513 if the checkbox (6) is checked or to step S1512 if the checkbox (6) is unchecked. In step S1512, the checked checkbox (5) is disabled, and the flow proceeds to step S1513. Because of this, even if the birth date is deselected from matching, at least the patient name is included for matching when the patient information is matched against the database.

In step S1513, the flow proceeds to step S1515 if the checkbox (1) is checked or to step S1514 if the checkbox (1) is unchecked. In step S1514, the checkbox (9) is unchecked and disabled. In contrast, in step S1515, the checkbox (9) is enabled. This prevents the database from being overwritten with a null patient name. In other words, the patient name in the database is prevented from being deleted.

A processing flow where access to checkboxes is controlled case by case is not limited to that shown in FIG. 16. Any processing flow that allows only the combinations of settings shown in the tables in FIG. 13B is acceptable.

As described above, with the GUI that automatically controls access to checkboxes, complicated but coherent condition settings can easily be achieved.

The present invention may also be realized by supplying a system or an apparatus with a recording medium storing software program code for realizing the function of the X-ray image display unit according to the first embodiment, and then causing the computer (CPU (central processing unit) or MPU (micro-processing unit)) of the system or the apparatus to read and execute the supplied program code.

The present invention may also be realized by supplying a system or an apparatus with a recording medium storing software program code for realizing the function of the present invention, and then causing the computer (CPU or MPU) of the system or the apparatus to read and execute the supplied program code.

In this case, the program code itself read from the recording medium realizes the function of the present invention.

The recording medium for supplying the program code includes, for example, a flexible disk, a hard disk, an optical disk, a magneto-optical disk, a CD-ROM, a CD-R, a magnetic tape, a non-volatile memory card, and a ROM.

As described above, the function of the present invention is achieved with the execution of the program code read by the computer. In addition, the function of the present invention may also be achieved by, for example, the OS (operating system) running on the computer that performs all or part of the processing according to the commands of the program code.

Furthermore, the function of the present invention may also be achieved such that the program code read from a recording medium is written to a memory provided in an expansion card disposed in the computer or an expansion unit connected to the computer, and then, for example, the CPU provided on the expansion card or the expansion unit performs all or part of the processing based on commands in the program code.

While the present invention has been described with reference to exemplary embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

This application claims priority from Japanese Patent Application No. 2004-029471 filed Feb. 5, 2004, which is hereby incorporated by reference herein.

What is claimed is:

1. An information processing method for registering additional information of an input image in a storage unit, the information processing method comprising:

receiving required check item conditions and matching item conditions specified by a user,
wherein the required check item conditions specify one or more items of additional information that are required for data registration, the one or more items of additional information specified by the required check item conditions are selected from a plurality of potential required additional information items; and
wherein the matching item conditions specify one or more items of additional information that are matched against corresponding items of pre-registered additional information, the one or more items of additional information specified by the matching item conditions are selected from a plurality of potential matching additional information items;

reading additional information of the input image;
deciding to register the additional information of the input image based on whether the additional information of the input image includes the one or more items of additional information selected from a plurality of potential required additional information items;
matching each of the one or more items of additional information of the input image specified by the one or more items of additional information selected from the plurality of potential matching additional information items against the corresponding items of pre-registered additional information; and
performing control to register the additional information of the input image when the additional information of the input image includes the one or more items of additional information selected from the plurality of potential required additional information items, and each of the one or more items of additional information of the input image specified by the one or more items of additional information selected from the plurality of potential matching additional information items matches the corresponding items of pre-registered additional information.

2. The information processing method according to claim 1, wherein the matching the additional information further comprises outputting a result of the matching.

3. The information processing method according to claim 1, wherein, the additional information of the input image is not registered if the one or more items of additional information of the input image specified by the matching item conditions and the corresponding items of pre-registered additional information do not match each other.

4. The information processing method according to claim 1, wherein the image is a medical image and the additional information includes at least two of a patient ID, a patient name, a patient sex, and a patient birth date.

5. The information processing method according to claim 4, wherein the plurality of potential matching additional information items includes at least one of patient ID, patient name, patient sex, and patient birth date.

6. The information processing method according to claim 5, wherein, if the matching item condition specifies one or more items of additional information that includes the patient name, the patient name is divided into strings by at least one delimiter, and matching is performed string by string.

7. The information processing method according to claim 6, wherein, if the patient name includes a middle name, the patient name is divided into three strings by two delimiters, and the matching is performed string by string.

8. The information processing method according to claim 5, wherein, if the matching item condition does not specify one or more items of additional information that includes the patient name and if the one or more items of additional information of the input image specified by the matching item conditions matches a first set of pre-registered additional information and the patient name associated with the additional information of the input image does not match a patient name associated with the first set of pre-registered additional information, the patient name associated with the additional information of the input image overwrites the patient name associated with the first set of pre-registered additional information.

9. A non-transitory computer-readable storage medium storing a control program for causing a computer to execute an information processing method comprising:
   receiving required check item conditions and matching item conditions specified by a user,
      wherein the required check item conditions specify one or more items of additional information that are required for data registration, the one or more items of additional information specified by the required check item conditions are selected from a plurality of potential required additional information items; and
      wherein the matching item conditions specify one or more items of additional information that are matched against corresponding items of pre-registered additional information, the one or more items of additional information specified by the matching item conditions are selected from a plurality of potential matching additional information items;
   reading additional information of an input image;
   deciding to register the additional information of the input image based on whether the additional information of the input image includes the one or more items of additional information selected from a plurality of potential required additional information items;
   matching each of the one or more items of additional information of the input image specified by the one or more items of additional information selected from the plurality of potential matching additional information items against the corresponding items of pre-registered additional information; and
   performing control to register the additional information of the input image when the additional information of the input image includes the one or more items of additional information selected from the plurality of potential required additional information items, and each of the one or more items of additional information of the input image specified by the one or more items of additional information selected from the plurality of potential matching additional information items matches the corresponding items of pre-registered additional information.

10. The information processing method according to claim 1, further comprising:
   restricting the plurality of potential matching additional information items to the one or more items of additional information specified by the required check item conditions.

11. The information processing method according to claim 1, wherein
   a first set of pre-registered additional information is all of the information associated with the corresponding items of pre-registered additional information that matches the one or more items of additional information of the input image specified by the matching item conditions;
   if (a) all of the one or more items of additional information of the input image specified by the matching item conditions matches corresponding information associated with the first set of pre-registered additional information, (b) the additional information of the input image includes a second set of information not specified by the matching item conditions, and (c) one or more items of the second set of information does not match corresponding information associated with the first set of pre-registered additional information, then the one or more items of the second set of information that do not match the corresponding information associated with the first set of pre-registered additional information overwrite the corresponding information associated with the first set of pre-registered additional information.

12. The information processing method according to claim 11, wherein
   the one or more items of the second set of information overwrites the corresponding information associated with the first set of pre-registered additional information if the second set of information is specified by the required check item conditions; and
   the one or more items of the second set of information do not overwrite the corresponding information associated with the first set of pre-registered additional information if the second set of information is not specified by the required check item conditions.

13. The information processing method according to claim 11, further comprising:
   receiving an overwrite check item condition specified by the user;
   wherein the second set of information overwrites the first set of corresponding information with the first set of pre-registered additional information if the second set of information is one or more of the items of additional information that are specified by the required check item conditions and the overwrite check item condition is in a first state; and
   the second set of information does not overwrite the first set of corresponding information with the first set of pre-registered additional information if the second set of information is not one or more of the items of additional information that are specified by the required check item conditions or the overwrite check item condition is in a second state.

14. The information processing method according to claim 11, wherein the second set of information is the patient name.

15. An information processing method for registering additional information of an input image in a storage unit, the information processing method comprising:
   receiving required check item conditions and matching item conditions specified by a user,
      wherein the required check item conditions specify one or more items of additional information that are required for data registration, the one or more items of additional information specified by the required check item conditions are selected from a plurality of potential required additional information items; and wherein the matching item conditions specify one or more items of additional information that are matched against corresponding items of pre-registered additional information, the one or more items of additional information specified by the matching item conditions are selected from a plurality of potential matching additional information items;

reading additional information of the input image;

deciding to register the additional information of the input image based on whether the additional information of the input image includes the one or more items of additional information selected from a plurality of potential required additional information items;

matching each of the one or more items of additional information of the input image specified by the one or more items of additional information selected from the plurality of potential matching additional information items against the corresponding items of pre-registered additional information; and performing control not to register the additional information of the input image when the additional information of the input image does not include the one or more items of additional information selected from the plurality of potential required additional information items.

16. A non-transitory computer-readable storage medium storing a control program for causing a computer to execute an information processing method for registering additional information of an input image in a storage unit comprising:

receiving required check item conditions and matching item conditions specified by a user, wherein the required check item conditions specify one or more items of additional information that are required for data registration, the one or more items of additional information specified by the required check item conditions are selected from a plurality of potential required additional information items; and wherein the matching item conditions specify one or more items of additional information that are matched against corresponding items of pre-registered additional information, the one or more items of additional information specified by the matching item conditions are selected from a plurality of potential matching additional information items;

reading additional information of the input image;

deciding to register the additional information of the input image based on whether the additional information of the input image includes the one or more items of additional information selected from a plurality of potential required additional information items;

matching each of the one or more items of additional information of the input image specified by the one or more items of additional information selected from the plurality of potential matching additional information items against the corresponding items of pre-registered additional information; and performing control not to register the additional information of the input image when the additional information of the input image does not include the one or more items of additional information selected from the plurality of potential required additional information items.

\* \* \* \* \*